United States Patent
Chait Auerbach et al.

(10) Patent No.: US 10,610,498 B2
(45) Date of Patent: Apr. 7, 2020

(54) ORAL VETERINARY COMPOSITION WITH GABAPENTIN

(71) Applicant: Jaime Samuel Chait Auerbach, Mexico City (MX)

(72) Inventors: Jaime Samuel Chait Auerbach, Mexico City (MX); Cliserio Perez Navarrete, Mexico City (MX)

(73) Assignee: Jaime Samuel Chait Auerbach (MX)

( * ) Notice: Subject to any disclaimer, the term of this patent is extended or adjusted under 35 U.S.C. 154(b) by 0 days.

(21) Appl. No.: 16/076,578

(22) PCT Filed: Dec. 2, 2016

(86) PCT No.: PCT/MX2016/000124
§ 371 (c)(1),
(2) Date: Aug. 8, 2018

(87) PCT Pub. No.: WO2017/095214
PCT Pub. Date: Jun. 8, 2017

(65) Prior Publication Data
US 2019/0046475 A1 Feb. 14, 2019

(30) Foreign Application Priority Data
Dec. 2, 2015 (MX) .......................... A/2015/016589

(51) Int. Cl.
| | | |
|---|---|---|
| A61K 31/138 | (2006.01) | |
| A61K 31/195 | (2006.01) | |
| A61K 31/135 | (2006.01) | |
| A61K 47/26 | (2006.01) | |
| A61P 25/04 | (2006.01) | |
| A61P 25/08 | (2006.01) | |
| A61K 9/20 | (2006.01) | |

(52) U.S. Cl.
CPC .......... *A61K 31/138* (2013.01); *A61K 9/2009* (2013.01); *A61K 9/2018* (2013.01); *A61K 9/2054* (2013.01); *A61K 9/2059* (2013.01); *A61K 9/2072* (2013.01); *A61K 31/135* (2013.01); *A61K 31/195* (2013.01); *A61K 47/26* (2013.01); *A61P 25/04* (2018.01); *A61P 25/08* (2018.01)

(58) Field of Classification Search
CPC combination set(s) only.
See application file for complete search history.

(56) References Cited

U.S. PATENT DOCUMENTS

| 2008/0014228 A1* | 1/2008 | Darmuzey | A61J 3/07 424/401 |
|---|---|---|---|
| 2010/0239668 A1* | 9/2010 | Kaplan | A61K 9/209 424/467 |
| 2013/0123245 A1 | 5/2013 | Coetzee et al. | |

FOREIGN PATENT DOCUMENTS

| MX | 223993 | 11/2004 |
|---|---|---|
| WO | 1999/12537 | 3/1999 |
| WO | 2000/053225 | 9/2000 |
| WO | 2006/123247 | 11/2006 |

OTHER PUBLICATIONS

Stein (Veterinary Anesthesia & Analgesia Support Group, Jun. 4, 2011, VASG Newer Options for Chronic Pain Management). (Year: 2011).*
DogHealth (LowchensAustralia.com, http://www.lowchensaustralia.com/health/prozac.htm, 2007). (Year: 2007).*
"Nota Farmacológica: Gabapentina para el dolor. Nueva evidencia surgida de datos no revelados Gabapentin for pain. New evidence from hidden data." Therapeutic letter, issue 75, Jul.-Dec. 2009.
"Intoxicaciones más frecuentes en pequeños animales"; Palabras clave: Intoxicación, Pequeños animales, Urgencias. Rev. AVEPA, 24(4) 231-239, 2004.
Jorge Mario Cruz Amaya1*, MV, PhD; Luis Mauricio Montoya Flórez MVZ2, "Toxicity with phenylbutazone in a horse: a case report*"; Fecha de recibido: 31 de enero de 2011; fecha de aceptado: 14 de junio de 2011.
Verrue C., C. , Mehuys E. , Boussery K. , Remon J.-P. & Petrovic M. (2011) Tablet-splitting: a common yet not so innocent practice. Journal of Advanced Nursing 67(1), 26-32. doi: 10.1111/j.1365-2648.2010.05477.x.
Glynn, Hayley Deanna, "Identifying and Alleviating Pain Associated With Routine Husbandry Procedures Performed on Pre and Post Weaning Dairy Calves"; 2012.
Terry, R.L., et al. "Pharmacokinetic profile and behavioral effects of gabapentin in the horse"; J. vet. Pharmacol. Therap. 33, 485-494. doi: 10.1111/j.1365-2885.2010.01161.x., 2010.
Laura D. Errante & Ognen A. C. Petroff, "Acute effects of gabapentin and pregabalin on rat forebrain cellular GABA, glutamate, and glutamine concentrations", Department of Neurology, Yale University School of Medicine, New Haven, CT 06520-8018, USA, Seizure 2003; 12: 300-306.
Minarda De la O-Arciniega, Beatriz Godinez-Chaparro, Uriah Guevara-López, Alma Rosa Cortés-Arroyo,§ Francisco Javier López-Muñoz, "Efecto antihiperalgésico de una combinación de morfina y gabapentina en dolor neuropático inducido por constricción crónica en rata"; Cir Ciruj 2007; 75: 363-369. Volumen 75, No. 5, septiembre-octubre 2007.
Hielm-Bjorkman HK, Rita H, Tulamo R-M. Psychometric testing of the helsinki chronic pain index by completion of a questionnaire in Finnish by owners of dogs with chronic signs of pain caused by osteoarthritis. Am J. Vet. Res. 70:727-734, 2009.

* cited by examiner

*Primary Examiner* — Umamaheswari Ramachandran
(74) *Attorney, Agent, or Firm* — Emerson, Thomson & Bennett, LLC; Roger D. Emerson; Peter R. Detorre (57) ABSTRACT

The present invention relates to a solid veterinary pharmaceutical composition, of oral administration comprising: a) a drug selected from gabapentin and/or fluoxetine or a pharmaceutically acceptable salt thereof, preferably gabapentin or an acceptable salt thereof in a concentration from 10 to 1000 mg; b) from 10% to 80% of the composition total weight of at least one silicon salt selected preferably from silicon dioxide, colloidal silicon dioxide, calcium silicate, magnesium silicate or combinations thereof; c) from 1% to 20% of the composition total weight of at least one polyoxyethylenated sorbitan ester, preferably selected from sorbitan monolaurate, sorbitan monooleate and sorbitan trioleate, or combinations thereof; and d) one or more pharmaceutically acceptable excipients; such that it is optimally prepared as a veterinary pharmaceutical product that exhibits safety and efficacy in mammalian animals, preferably in companion animals.

10 Claims, 3 Drawing Sheets

ORAL VETERINARY COMPOSITION WITH GABAPENTIN

FIELD OF THE INVENTION

The present invention relates to a stable composition comprising a drug selected from gabapentin and/or fluoxetine or a pharmaceutically acceptable salt thereof, useful for the prevention and/or treatment of mild, moderate or severe pain and epilepsy, wherein the composition comprises at least one silicon salt selected preferably from silicon dioxide, colloidal silicon dioxide, calcium silicate, magnesium silicate or combinations thereof; at least one polyoxyethylenated sorbitan ester, selected preferably from sorbitan monolaurate, sorbitan monooleate and sorbitan trioleate, or combinations thereof; and one or more pharmaceutically acceptable excipients; in such a way that it is optimally prepared as a veterinary pharmaceutical product that exhibits safety and efficacy in mammalian animals, preferably in a non-restrictive manner in pet animals.

BACKGROUND

Gabapentin is a drug that since 1993 is used for the adjuvant treatment of epilepsy. In 1998, two double-blind, randomized controlled trials suggested that gabapentin had mild analgesic effects on pain caused by diabetic peripheral neuropathy and postherpetic neuralgia. Subsequently, the use of gabapentin appeared for unapproved indications of pain treatment, migraine and even as a mood stabilizer.

In this way, the promotion of indications for the pain treatment by gabapentin was supported by the publication and selective citation of studies with favorable results, extending its application to neuropathic pain, gradually becoming the most durable market for the use of gabapentin, reinforced by the practice guidelines that referred to gabapentin as the first line of treatment. (Evidence: Update in Ambulatory Practice, April/June 2010. Vol. 13 No. 2).

Gabapentin is probably the most studied drug in its basic and clinical aspects, in order to elucidate its mechanism of action and establish its real clinical efficacy. It has been postulated that gabapentin exerts its effects through three different mechanisms: the facilitation of gabaergic transmission, the decrease in gabaergic transmission, the decrease of various ion channels. However, the available evidence on how gabapentin acts on such pathways is variable and often contradictory.

Gabapentin is an analogue of gamma-aminobutyric acid (GABA), it has been described that gabapentin is an agonist of the GABAB gb1a-gb2 heterodimer that is coupled to a subtype of potassium channel called Kir 3,1/3,2 (internal rectification of potassium channels). The consequence of this action of gabapentin would be a nervous hyperpolarization with a decrease in bioelectric activity. It has also been shown that gabapentin increases the cerebral content of GABA acutely and chronically, probably through the non-vesicular release of this neurotransmitter. (Baños J E, Malouf J., 2002).

A second possibility is that gabapentin acts by preventing the activation of glutamate receptors, especially NMDA, by direct or indirect actions. These receptors are complex structures and, for example, can be acted pharmacologically on the binding site of the agonist (glutamate), the associated ion channel or the binding site of glycine. Gabapentin does not act on the first two, but there are some indirect studies that indicate that it could do so on the third, since its effects are reversed by the D-serine administration, an agonist at the glycine binding site. The result would be a decrease in the activation of such receptors by glutamate. Additionally, electrophysiological studies have shown how gabapentin can even reduce the release of glutamate in the posterior horn of the spinal cord.

Perhaps, the most peculiar mechanism of action of gabapentin is the binding to a specific site, the $\alpha 2\delta$ subunit, present in all the voltage-dependent calcium channels (CCDV) that have been studied until today. The physiological role of this subunit is to increase the functional expression of calcium channel complexes. At present, three distinct subunits have been characterized, called $\alpha 2\delta$-1, $\alpha 2\delta$-2 and $\alpha 2\delta$-3, but gabapentin binds only to the first two, especially at $\alpha 2\delta$-1. Thus, by attaching to the $\alpha 2\delta$ subunit, gabapentin blocks the calcium entry through the presynaptic calcium channels, especially P and Q, but also L. In this way, the neurotransmitter release in various areas of the central nervous system would be inhibited.

Pain is defined as an unpleasant sensory and emotional experience associated with real or potential tissue injury, becoming the most frequent clinical manifestation.

The pharmacological treatments for pain described in the state of the art are integrated by three categories of medications: non-steroidal anti-inflammatory drugs (NSAIDs), opioid analgesics and adjuvant analgesics.

Among the main NSAIDs are: acetaminophen, lysine acetylsalicylate, acetylsalicylic acid, mefenamic acid, diclofenac, etodolac, fenoprofen, ibuprofen, indomethacin, ketoprofen, ketorolac, meclofenamate, naproxen, sulindac, among others.

Opioid analgesics act on opioid receptors located in the Central Nervous System and in the spinal cord by inhibiting the adenylyl cyclase enzyme, reducing the amount of intracellular cAMP. They open the K+ ion channels and inhibit the Ca2+ channels. Among the main opioid analgesics are: anilinopiperidine, diphenylmethane, phenylpiperidine, oripavine, morphinan, among others.

Adjuvant analgesics are those whose main pharmacological action is not analgesia, however, they are generally used in a complementary way to the pain treatment to increase the analgesic effect of other drugs, decreasing their toxicity, the requirements of opiates, improving pain associated symptoms, fighting adverse effects of analgesics, allowing pain relief and concomitant psychological disorders. Gabapentin and caffeine are among the adjuvant analgesics useful for the pain treatment effectively.

The pain treatment in animals by the veterinarian is not only an ethical and humanitarian practice, but also based on limiting the serious physiopathological consequences derived from a painful stimulus. It is known that untreated pain causes distress, prolongs the recovery and hospitalization time, hinders the healing process, can lead to self-mutilations, causes hypoxia/hypercarbia, increases cellular catabolism, produces neuronal sensitization and, ultimately, increases the morbidity and mortality of patients.

Both narcotic analgesics (opioids) and NSAIDs are very effective in treating perioperative pain of moderate to severe intensity, however, one of the problems when using NSAIDs in animals is that there is a likelihood that they will suffer some type of poisoning.

In the case of paracetamol the recommended dose for dogs is 15 mg/kg/8 h, the toxic dose in cats 50 mg/kg and in dogs 150 mg/kg. Cats have very low levels of glucuronyl transferase and limited activity to conjugate sulfates, which oxidized by CP450 give rise to a toxic metabolite: N-acetyl-para-benzoquinoneimine (NAPQ). This compound, covalently linked with macromolecules, is involved in the hemoglobin transformation to methaemoglobin, forming Heinz bodies, increasing the osmotic fragility of erythrocytes, and leading to hemolysis, anemia and, particularly, cats are especially sensitive to acute renal failure.

In the case of acetylsalicylic acid, the therapeutic and toxic doses are very close, being the anti-inflammatory dose of 25 mg/kg/8 h and the analgesic of 10-20 mg/kg/8 h in dogs. In this species, vomiting and gastric ulcers have been described due to the intake of doses greater than 50 mg/kg/24 h and 100 mg/kg/24 h for 1 and 4 weeks respectively. Cats have a defect in the activity of the glucuronosyl transferase enzyme, so they are more susceptible to poisoning. The analgesic and toxic doses in this species are 10 mg/Kg/48 h, and 80-120 mg/Kg/24 h for 10 and 12 days respectively. The product is absorbed at the gastric and intestinal level, undergoes hepatic metabolism and is excreted via the kidneys, it is bound by 90% to plasma proteins.

Clinical condition is mainly due to the inhibition of prostaglandins, causing effects at digestive, platelet and renal levels. The acute condition occurs 4-6 hours after ingestion. It is characterized by depression, anorexia, hyperthermia, hyperglycemia and glycosuria, vomiting, hematemesis and tachypnea (because salicylates increase oxygen consumption, $CO_2$ production at striated muscle level and stimulate the respiratory center of the bulb). This situation can lead to an alteration of the acid-base state, and finally lead to acute renal failure, weakness, coma and non-cardiogenic pulmonary edema. The chronic condition is characterized by gastric ulcers with or without perforation, toxic hepatitis, anemia and delay in bleeding times, due to inhibition of the bone marrow. In cats, nausea and vomiting, respiratory depression and metabolic acidosis, hyperthermia, seizures and coma, toxic hepatitis, Heinz body anemia and thrombocytopenia are observed. Hypernatremia and hypokalemia can also be observed (Daza M A, 2004).

The use of phenylbutazone in horses for the claudication treatment (2 g/12 h/IV for 8 days) has caused gastric ulcers and necrotizing colitis with protein loss.

NSAIDs cause nephropathy by inhibiting the synthesis of vasopressor prostaglandins that regulate renal blood flow, glomerular filtration, tubular ion transport, renin release, and water metabolism.

The gastric and intestinal lesions caused by phenylbutazone are the result of microvascular injury and the decrease in mucus production due to low concentrations of prostaglandins. By inhibiting the metabolic pathway of arachidonic acid by cyclooxygenase blocking, the lipoxygenase pathway is increased, which increases the leukotrienes, hydroperoxy-eicosatetraenoic acids and free radicals which in turn are also gastrolesive. (Amaya, 2011)

In patent documents WO99/12537 and WO2000053225 refer to the combination of naproxen with gabapentin, integrating studies in rats by parenteral administration.

In the state of the art, it was found that the patent MX223993 refers to the use of pregabalin or gabapentin for the pain treatment, however, said document and the commercialized products derived from it, are focused on the pain treatment in humans, managing therapeutically required doses specific for humans. On the other hand, the patent application WO2006123247 refers to a combination for veterinary use comprising the combination of gabapentin and/or pregabalin with carprofen for the pain treatment and/or inflammation, especially in dogs, cats and horses. This patent application describes the oral dosage forms, indicating various excipients, however it does not specify any formula suitable for oral administration specific for animals, besides that the tests of the drug combination is carried out by parenteral administration.

In this way, the administration of combinations of two or more NSAIDs, or together with corticosteroids, potentially increases their toxicity. Besides this, the ignorance of the condition of liver or kidney functionality of pets, the treatment with NSAIDs is highly dangerous, however, these drugs are commonly used by veterinarians or animal owners.

Meanwhile, the use of gabapentin for the pain treatment and epilepsy has been focused on human use, even though all the studies have been carried out on animals (mainly rodents), little has been reported about its veterinary application orally and there are no compositions that provide safety and effectiveness when administered in animals, such as pets.

It is necessary to have compositions that, in addition to being stable, preserve efficacy after oral administration, that is, that allow the control of pain or epileptic events in pet animals without presenting the toxic effects that NSAIDs can produce.

Likewise, there is a need to administer different doses, according to the variety of size and weight of the companion animals, so, the segmentation of the tablets is the most viable option because they allow adjustments in the medication dose, easier swallowing and cost savings for both the owner of the animal and health providers.

However, during the manufacturing process the segmentation of the tablet presents drawbacks, since it can be difficult to carry out due to its hardness, the segments obtained are usually of different size, an amount can be lost during the segmentation (Verrue, 2010) so that the homogeneous distribution of the active principle of each segment can be questionable.

However, conduction of relevant analyzes such as assessment, hardness and bioavailability allow demonstrating that said drawbacks will not occur and each segment obtained from the tablet will have the same physical, chemical and therapeutic characteristics.

OBJECT OF THE INVENTION

The object of the present invention is to provide solid oral pharmaceutical compositions for veterinary use comprising a drug selected from gabapentin and/or fluoxetine or a pharmaceutically acceptable salt thereof, useful for the prevention and/or treatment of mild, moderate or severe pain and epilepsy; in addition, wherein the compositions are optimally prepared as a veterinary pharmaceutical product that exhibits safety and efficacy in mammalian animals, preferably not limited to companion animals.

DETAILED DESCRIPTION OF THE INVENTION

The present invention relates to a solid veterinary pharmaceutical composition for oral administration comprising:

a) a drug selected from gabapentin and/or fluoxetine or an acceptable salt thereof in a concentration of 1 to 1000 mg; b) from 10% to 80% of the composition total weight of at least one silicon salt selected preferably from silicon dioxide, colloidal silicon dioxide, calcium silicate, magnesium silicate or combinations thereof; c) from 1% to 20% of the composition total weight of at least one polyoxyethylenated sorbitan ester, preferably selected from sorbitan monolaurate, sorbitan monooleate and sorbitan trioleate, or combinations thereof; and d) one or more pharmaceutically acceptable excipients; such that it is optimally prepared as a veterinary pharmaceutical product that exhibits safety and efficacy in mammalian animals, preferably not limited to companion animals.

The solid oral veterinary pharmaceutical composition with potentiated analgesic effect comprises: a) gabapentin and/or an acceptable salt thereof; b) at least one silicon salt; c) at least one disintegrant; d) at least one anti-binding agent; e) at least one diluent, f) at least one lubricant and, optionally, g) at least one colorant.

Where the disintegrant may be at least one of the following excipients: microcrystalline cellulose, alginic acid, sodium croscarmellose, crospovidone, hydroxypropyl cellulose, potassium polacrilin, pullulan, starch, sodium starch glycolate, gelatinized starch, among others.

Where the anti-binding agent can be at least one of the following excipients: calcium silicate, magnesium silicate, colloidal silicon dioxide, talc, hydrophobic colloidal silica, among others.

Where the diluent can be at least one of the following excipients: calcium carbonate, dibasic calcium phosphate, tribasic calcium phosphate, calcium sulfate, microcrystalline cellulose, dextrose, fructose, kaolin, mannitol, lactose, maltodextrin, maltose, starch, sorbitol, sucrose, among others.

Where the lubricant may be at least one of the following excipients: calcium stearate, magnesium stearate, polyethylene glycol, sodium lauryl sulfate, sodium stearyl fumarate, sorbitan monolaurate, sorbitan monopalmitate, polysorbate, talc, starch, stearic acid, ether oleyl polyoxyl 10, polyoxyl 35 castor oil, zinc stearate, among others.

Where the colorant can be at least one of the following excipients: caramel, ferric oxide, red, yellow, titanium oxide, carmoisine, bluish black of naphthol, erythrosin, amaranth or mixtures.

The inclusion of at least one drying agent in the composition resulted, in an unexpected manner, in obtaining a composition with greater stability compared to a composition obtained without the inclusion of said component.

The drying agent is selected in a non-restrictive manner from calcium chloride, silicon dioxide and calcium sulfate, preferably silicon dioxide.

It was obtained as a product of the present invention a composition of high stability, which additionally potentiates the analgesic effect of gabapentin when administered orally to animals, preferably not limited to companion animals.

Within the state of the art, is reported the use of gabapentin for the pain treatment in humans (MX223993); the combination of gabapentin and meloxicam, but focus on the pain treatment by castration, dehorning and marking of ruminant and pre-ruminant animals (US2013123245), however, the inclusion of meloxicam, which is an NSAID, a composition is obtained with a high level of toxicity for animals that has an analgesic effect; additionally, the studies described in said document were carried out in ruminant calves and cattle and do not describe a specific composition.

Another combination described in the state of the art comprises gabapentin and carprofen for use in cats, dogs and horses suffering from pain or inflammation (WO2006123247); as reported in the state of the art, are the patents referenced above as well as products commercially available pharmaceuticals, however, is not described in the state of the art an oral pharmaceutical composition for the pain prevention and/or treatment or epilepsy for veterinary use.

Within the literature regarding the use of gabapentin is a series of articles that mention it in studies for veterinary species. Among which there are: studies to determine the effectiveness of an analgesic method in which is administrated meloxicam (1 mg/Kg oral), gabapentin (15 mg/Kg oral), meloxicam (1 mg/Kg intravenous), gabapentin (15 mg/Kg oral), flunixin (2.2 mg/Kg intravenous) and a placebo for the treatment of calf dehorning, obtaining that gabapentin alone or with meloxicam significantly decreases the concentration of substance P and the average daily gain compared to the control (Glynn H D, 2012).

In addition, studies have been conducted to determine the pharmacokinetic and behavioral profile in horses for gabapentin, for which 20 mg/kg of gabapentin was administered orally or intravenously to six horses using a randomized cross-over design, the concentration of the compound in plasma was measured in samples collected in 0-48 hours post-administration using a mass spectrometer by liquid chromatography, obtaining a half-life of 8.5 h IV and 7.7 h p.o. Gabapentin administered orally had a relatively low absorption (bioavailability $16.2^+$-2.8%); in terms of behavior, drinking water was consistently greater and staying at rest was lower in the animals that took intravenous gabapentin. Another study about the pharmacokinetics of gabapentin in horses shows that when administering a dose of 5 mg/Kg oral it is quickly absorbed and with a half-life of 3.4 h, and when compared said results with those obtained in humans, rats and monkeys, the Cmax is higher in these than in horses, which also indicates that the absorption of gabapentin is relatively slow and rapidly metabolized in horses, unlike other species, and in the case of the half-life this is relatively similar to that reported in dogs (3.4 h) (Terry R L, et al., 2010).

There is a study in which gabapentin is administered intraperitoneally in rats 100-1000 mg/kg, after administration the rats eat and drink freely, after two hours they are administered 100 mg/kg of phenobarbital and 0.4 ml 2N of 3-mercaptopropanoic acid, and the brain of the animal is obtained by separating it from the cerebellum and freezing it with liquid nitrogen, the blood is also collected from the body, when performing the analysis of the samples it was obtained that the gabapentin and its isoform pregabalin with antiepileptic effects decrease the cellular concentrations of glutamate (0.6-0.9% mN, 4-7%), which indicates that although the decrease was modest, these compounds could decrease cortical glutamate associated with epilepsy states (Errante L D and Petroff O A C, 2003).

Another article of interest is that in which studies are done with gabapentin to evaluate its functionality in the treatment of neuropathic pain, in that article it is administered subcutaneously individually morphine 3.2 mg/Kg and gabapentin 17.8 mg/Kg reaching its maximum effect at 60 minutes post-treatment, producing an antihyperalgesic effect of 51.7% and 55%. While the combined administration produced an almost total antihyperalgesic effect at 30 minutes (96.7%) and 100% at 60 minutes (Arciniega M O, et al., 2007).

For the development of this invention, studies were carried out to determine the safest and most effective dose and veterinary composition in order to provide a representative improvement to the existing compositions in the state of the art, the effectiveness of the composition being tested in two main treatments, the pain treatment and epilepsy.

The present invention relates to various veterinary pharmaceutical compositions for the oral administration of gabapentin, among which are, but are not limited to: tablets, sublingual tablet, chewable tablets, modified-release tablets, bolus, hard and soft gelatin capsules, powder, granules and/or effervescent tablets; preferably segmentable tablets that comprise the same physical, chemical and therapeutic characteristics in each segment obtained.

The above described compositions contain at least one pharmaceutically acceptable excipient selected from the following group: release polymers, binder, lubricant, solvent, diluent, dissolving modifying agent, desiccant, colorant, glidant, solubility enhancing agent, disintegrant, superdisintegrant, anti-binding agent, among others known in pharmaceutical practice.

In the following, the compositions used during the development of the invention are described by way of illustrative, but not limiting, examples:

EXAMPLES

Example 1. Composition of Gabapentin with 50% Silicon Salt and 14% Polyoxyethylenated Sorbitan Ester

| Components | Content % w/w | | | |
|---|---|---|---|---|
|  | A | B | C | D |
| Gabapentin | 5 | 5 | 5 | 5 |
| Silicon dioxide | 50 | 0 | 0 | 0 |
| Colloidal silicon dioxide | 0 | 50 | 0 | 0 |
| Calcium silicate | 0 | 0 | 50 | 0 |
| Magnesium silicate | 0 | 0 | 0 | 50 |
| Mannitol | 10 | 10 | 10 | 10 |
| Cellulose | 8 | 8 | 8 | 8 |
| Sodium croscarmellose | 5.9 | 5.9 | 5.9 | 5.9 |
| Crospovidone | 5 | 5 | 5 | 5 |
| Sorbitan monolaurate | 14 | 14 | 14 | 14 |
| Talc | 2 | 2 | 2 | 2 |
| Colorant | 0.1 | 0.1 | 0.1 | 0.1 |

Example 2. Composition of Gabapentin with 10% Silicon Salt

| Components | Content % w/w |
|---|---|
| Gabapentin | 5 |
| Colloidal silicon dioxide | 10 |
| Mannitol | 20 |
| Cellulose | 15 |
| Sodium croscarmellose | 12.9 |
| Crospovidone | 5 |
| Sorbitan monolaurate | 30 |
| Talc | 2 |
| Colorant | 0.1 |

Example 3. Composition of Gabapentin with 10% Desiccating Agent

| Components | Content % |
|---|---|
| Gabapentin | 5 |
| Silicon dioxide | 10 |
| Lactose | 40 |
| Cellulose | 20.9 |
| Hydroxypropylmethyl cellulose | 18 |
| Povidone | 3 |
| Sodium stearyl fumarate | 2 |
| Sodium lauryl sulfate | 1 |
| Colorant | 0.1 |

Example 4. Composition of Gabapentin with 80% Desiccating Agent

| Components | Content % |
|---|---|
| Gabapentin | 5 |
| Silicon dioxide | 80 |
| Lactose | 8.3 |
| Cellulose | 5 |
| Hydroxypropylmethyl cellulose | 0 |
| Povidone | 1 |
| Magnesium stearate | 0.5 |
| Talc | 0.1 |
| Colorant | 0.1 |

Example 5. Composition of Fluoxetine with 10% Silicon Salt

| Components | Content % w/w |
|---|---|
| Fluoxetine | 1 |
| Colloidal silicon dioxide | 10 |
| Mannitol | 24 |
| Cellulose | 15 |
| Sodium croscarmellose | 12.9 |
| Crospovidone | 5 |
| Sorbitan monolaurate | 30 |
| Talc | 2 |
| Colorant | 0.1 |

Efficiency Evaluation of the Composition in the Treatment of Epilepsy.

In order to comply with the various objectives of the present invention, studies were carried out to demonstrate the efficacy of gabapentin as treatment against idiopathic epilepsy in dogs, in said studies participated 30 animals of different races, aged from 1 to 5 years, variable weights and diagnosed with idiopathic epilepsy; the animals that had diseases were discarded and the following groups were formed:

a) G0-E Group: treated with phenobarbital at dose of 2 mg/Kg of body weight, every 12 hours.

b) G1-E Study Group: treated with gabapentin of 10 mg/Kg of body weight, divided 3 times a day by oral administration.

c) G2-E Study Group: treated with gabapentin of 20 mg/Kg of body weight, divided 3 times a day by oral administration.

Patients were monitored for 3 consecutive months, quantifying seizure episodes for each of the patients, obtaining the following:

TABLE 1

Evaluation of Gabapentin and Phenobarbital for the treatment of epilepsy (seizure number)

| Group | Patient | Seizure number per month prior to the study | Seizure number per month after the study |
|---|---|---|---|
| G0-E | 0-E-I | 2 | 0 |
| | 0-E-II | 1 | 1 |
| | 0-E-III | 3 | 0 |
| | 0-E-IV | 11 | 4 |
| | 0-E-V | 13 | 1 |
| | 0-E-VI | 2 | 0 |
| | 0-E-VII | 8 | 0 |
| | 0-E-VIII | 7 | 0 |
| | 0-E-IX | 2 | 1 |
| | 0-E-X | 10 | 1 |
| G1-E | 1-E-I | 11 | 0 |
| | 1-E-II | 4 | RESCUED |
| | 1-E-III | 5 | 0 |
| | 1-E-IV | 8 | RESCUED |
| | 1-E-V | 5 | 1 |
| | 1-E-VI | 10 | 0 |
| | 1-E-VII | 6 | 0 |
| | 1-E-VIII | 1 | 0 |
| | 1-E-IX | 3 | 0 |
| | 1-E-X | 9 | 0 |
| G2-E | 2-E-I | 8 | 2 |
| | 2-E-II | 2 | 0 |
| | 2-E-III | 12 | 1 |
| | 2-E-IV | 2 | 1 |
| | 2-E-V | 8 | 0 |
| | 2-E-VI | 8 | RESCUED |
| | 2-E-VII | 6 | 0 |
| | 2-E-VIII | 4 | 3 |
| | 2-E-IX | 4 | 0 |
| | 2-E-X | 3 | 2 |

Figure 1:
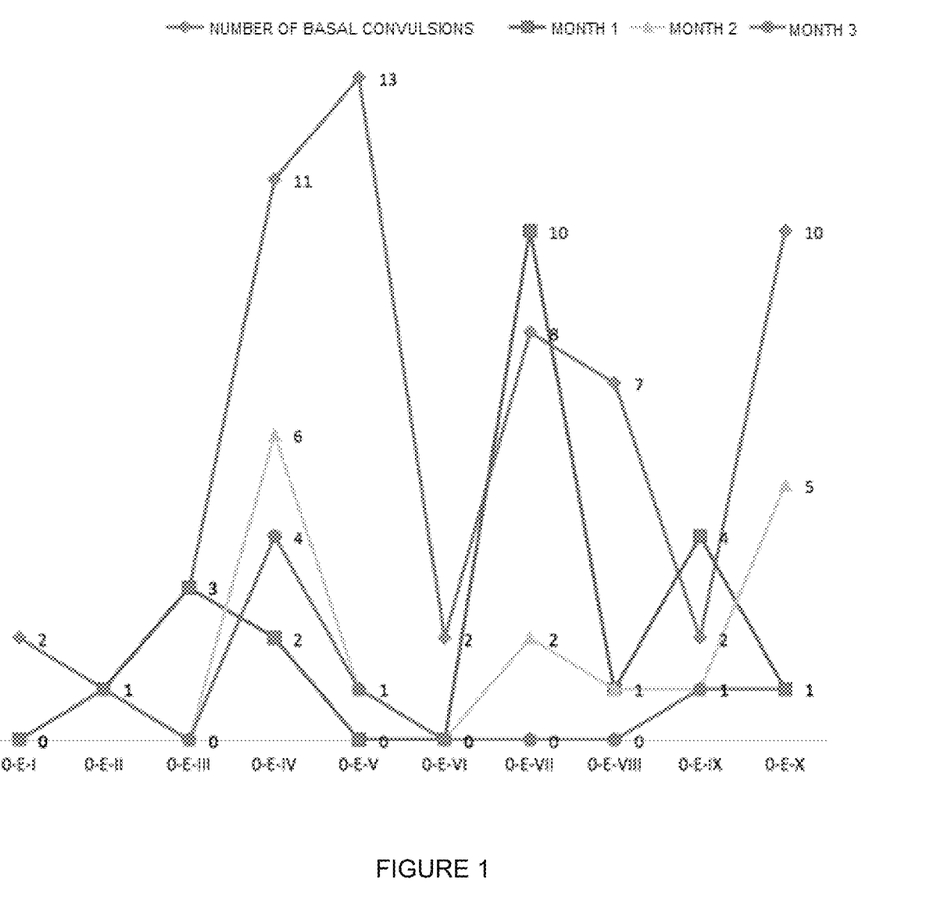
FIG. 1. Graph of the seizure number after administration of phenobarbital to the G0-E group.
Figure 2:
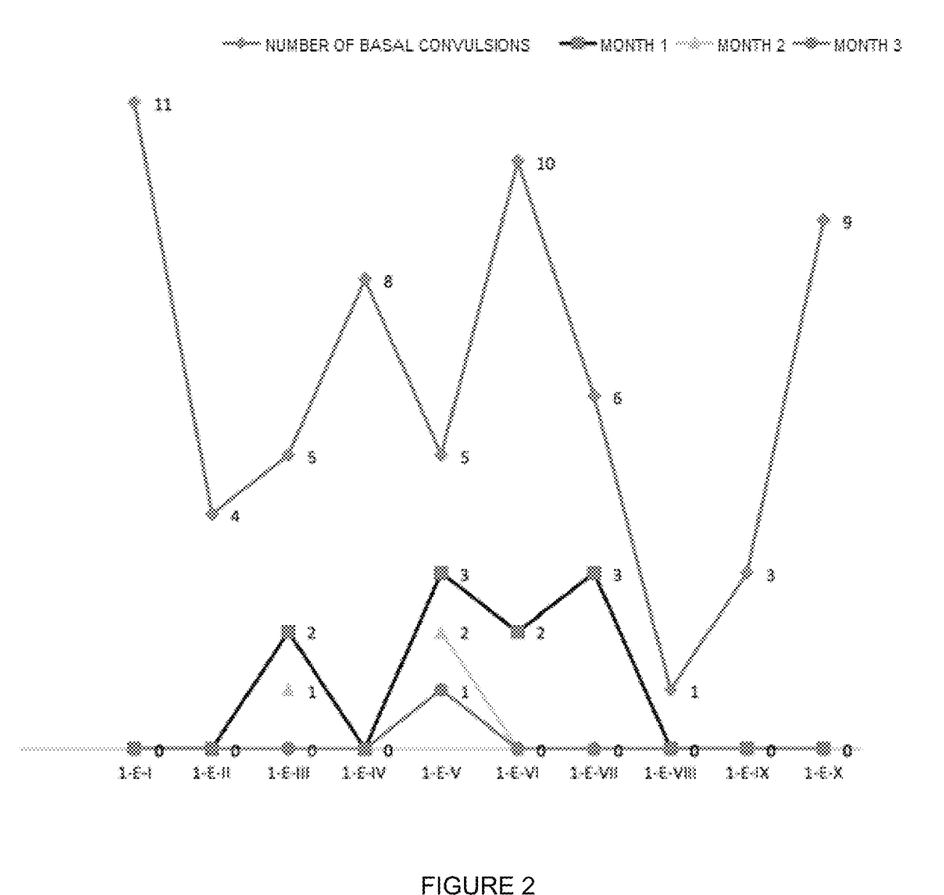
FIG. 2. Graph of the seizure number after administration of gabapentin in a dose of 10 mg/Kg of weight divided 3 times a day, to the G1-E group.
Figure 3:
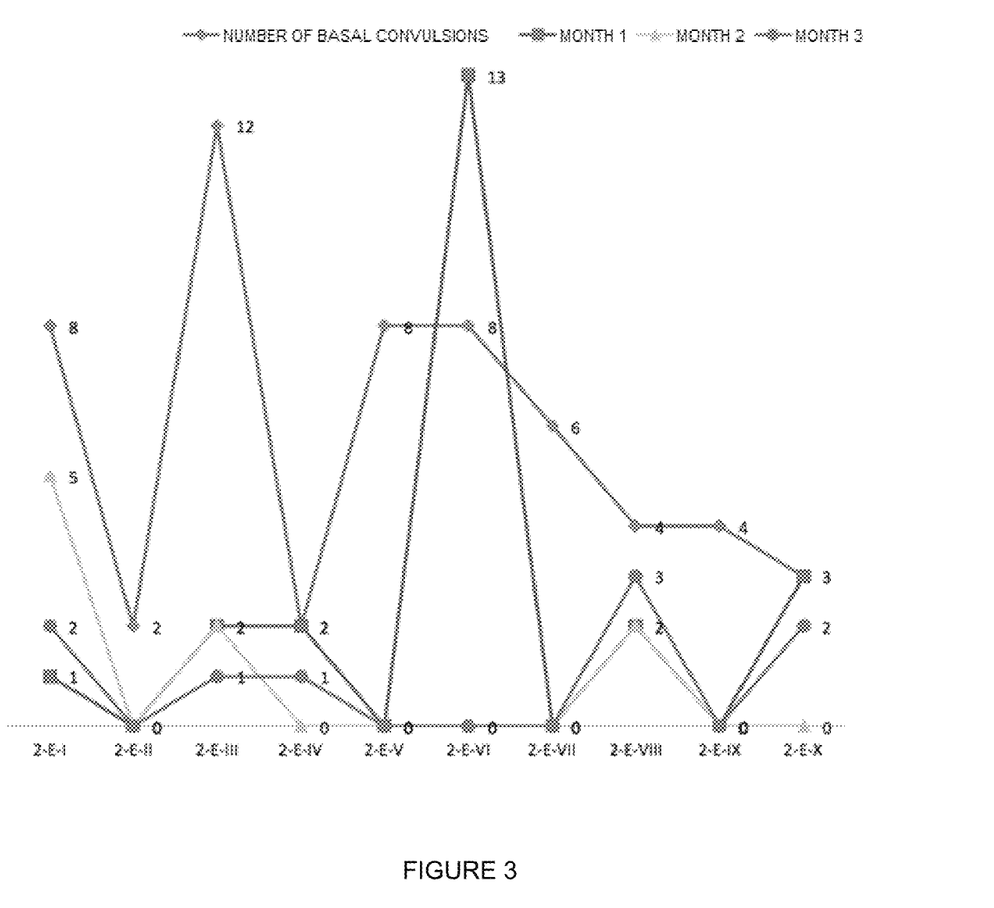
FIG. 3. Graph of the seizure number after administration of gabapentin in a dose of 20 mg/Kg of weight divided 3 times a day, to the G2-E group.

FIG. 1 shows the seizure number obtained by the administration of phenobarbital, while FIGS. 2 and 3 show the effect on the seizure number with oral administration of gabapentin in doses of 10 mg/kg and 20 mg/kg, respectively. From these results, it is important to highlight that the administration of oral compositions in doses evaluated, allows a control of seizure episodes, being unexpectedly, the dose of 10 mg/kg, the concentration that best result shows with a significant reduction of seizures at the month 3 of treatment.

Given the previous result, Table 2 shows the changes observed in the seizures of the patients in each group, as well as the clinical adverse effects that were observed during the treatment.

TABLE 2

Evaluation of Gabapentin and Phenobarbital for the treatment of epilepsy (changes and adverse effects)

| Group | Patient | Changes in the type of seizure | Clinical adverse effects observed |
|---|---|---|---|
| G0-E | 0-E-I | NONE | LIGHT SEDATION |
| | 0-E-II | PARTIAL CONVULSIONS | NONE |
| | 0-E-III | NONE | NONE |
| | 0-E-IV | CLONIC TONIC | NONE |
| | 0-E-V | CLONIC TONIC | HYPER-EXCITATION |
| | 0-E-VI | NONE | NONE |
| | 0-E-VII | PARTIAL CONVULSIONS | LIGHT SEDATION |
| | 0-E-VIII | CLONIC TONIC | NONE |
| | 0-E-IX | PARTIAL CONVULSIONS | NONE |
| | 0-E-X | PARTIAL CONVULSIONS | LIGHT SEDATION |
| G1-E | 1-E-I | NONE | NONE |
| | 1-E-II | NONE | NONE |
| | 1-E-III | PARTIAL CONVULSIONS | NONE |
| | 1-E-IV | NONE | NONE |
| | 1-E-V | PARTIAL CONVULSIONS | LIGHT SEDATION |
| | 1-E-VI | PARTIAL CONVULSIONS | NONE |
| | 1-E-VII | PARTIAL CONVULSIONS | NONE |
| | 1-E-VIII | NONE | NONE |
| | 1-E-IX | NONE | NONE |
| | 1-E-X | NONE | NONE |
| G2-E | 2-E-I | PARTIAL CONVULSIONS | LIGHT SEDATION |
| | 2-E-II | NONE | NONE |
| | 2-E-III | CLONIC TONIC | SOMNOLENCE |
| | 2-E-IV | CLONIC TONIC | NONE |
| | 2-E-V | NONE | NONE |
| | 2-E-VI | PARTIAL CONVULSIONS | LIGHT SEDATION |
| | 2-E-VII | NONE | LIGHT SEDATION |
| | 2-E-VIII | CLONIC TONIC | NONE |
| | 2-E-IX | NONE | NONE |
| | 2-E-X | PARTIAL CONVULSIONS | NONE |

It is clear that the reduction of the treatment dose in the composition shows less adverse effects than those obtained by the administration of the dose of 20 mg/Kg, additionally and unexpectedly, has less adverse effects than the composition containing phenobarbital.

Efficiency Evaluation of the Composition in the Pain Treatment.

In addition to the tests performed for the treatment of epilepsy, the effect of gabapentin in the pain treatment in dogs caused by osteoarthritis was evaluated, 30 animals of race, age, weight and variable sex were used, with 3/5 of body condition and clinical and radiological signs from moderate to severe of osteoarthritis, according to the Bioarth scale. Two study groups were formed:

a) G0-D Group: treated with fluoxetine at dose of 1 mg/Kg of body weight, every 12 hours, orally.

b) G1-D Group: treated with gabapentin of 1.5-10 mg/Kg of body weight, every 12 hours, orally.

The dogs were monitored 8 consecutive weeks by applying the questionnaires of the Subjective Clinical Evaluation System, Liverpool Osteoarthritis in Dogs and the Helsinki Chronic Pain Index to the owners of the dogs, before and after administration of the treatments.

The Subjective Clinical Evaluation System includes the following evaluation points:

1) Claudication: (0) in normal statics and walking normally, (1) in normal statics and slight claudication when walking (barely noticeable), (2) in normal statics, but moderate claudication when walking (raises the affected limb several times), (3) abnormal posture in static and severe claudication when walking (does not lean on the affected limb) and (4) reluctant to get up and does not take more than 5 steps.

2) Posture: (0) is maintained in a normal manner on all members at rest and when walking, (1) is maintained in a normal way at rest, but when walking gives preference to the affected member, (2) change of position at rest and when walking, (3) change of position at rest and does not lean on the affected limb when walking and (4) does not lean on the affected limb at rest or when walking.

3) Mobility of the affected joint: (0) No limitation of movement and no crepitus is palpable, (1) slight decrease in range of motion (10-20%), no crepitus is palpable, (2) slight decrease in range of motion (10-20%) with palpable crepitation, (3) moderate decrease in range of motion (20-50%) and (4) severe decrease in range of motion (>50%) with palpable crepitus.

4) Hold the contralateral limb high: (0) quickly accept to raise the contralateral limb, (1) offer resistance to the contralateral limb elevation, but maintain its weight on the affected limb for more than one minute, (2) offer moderate resistance to the elevation of the contralateral limb and replaces it after 30 seconds, (3) it offers resistance to the elevation of the contralateral limb and replaces it after 10 seconds and (4) refuses to elevate the contralateral limb.

5) Pain sign in the affected joint: (0) no response, (1) mild response (turns the head towards the affected joint), (2) moderate response (removes the affected joint member), (3) severe response (vocalizes and is aggressive) and (4) does not allow manipulation or palpation of the affected joint.

The results obtained are presented as global observations made with the Subjective Clinical Evaluation System expressed in Medians±EE, to these results the Wilcoxon ranks test was performed using the SPSS Statistics program. Statistically significant values were considered for a level of $p<0.05$.

TABLE 2

Evaluation of Gabapentin and Fluoxetine for the pain treatment

| GROUP | WEEK 0 | WEEK 4 | WEEK 8 |
|---|---|---|---|
| G0-D | 8.5 ± 0.51 | 8.5 ± 1.19 | 8 ± 1.79 |
| G1-D | 9 ± 0.86 | 4 ± 1.02 | 6 ± 0.73 |

The results of the global observations made by the owners with the Liverpool Osteoarthritis in Dogs questionnaire expressed in Medians±EE are presented in Table 3. The Wilcoxon ranks test was performed using the SPSS Statistics program considering statistically significant values for a level of $p<0.05$.

TABLE 3

Evaluation of Gabapentin and Fluoxetine for the pain treatment. Questionnaire Liverpool Osteoarthritis in Dogs

| TIME | G0-D | G1-D |
|---|---|---|
| WEEK 0 | 26 ± 2.2 | 27 ± 2.85 |
| WEEK 1 | 23.5 ± 5.4 | 24 ± 2.26 |
| WEEK 2 | 26 ± 5.19 | 22 ± 2.35 |
| WEEK 3 | 22.5 ± 4.52 | 23 ± 3.15 |
| WEEK 4 | 22.5 ± 4.38 | 22 ± 3.56 |
| WEEK 5 | 23 ± 2.95 | 26 ± 3.15 |
| WEEK 6 | 23 ± 2.56 | 26 ± 2.86 |
| WEEK 7 | 22.5 ± 1.95 | 23 ± 2.67 |
| WEEK 8 | 20.5 ± 1.35 | 20 ± 2.35 |

The results of the global observations made by the owners with the Helsinki Chronic Pain Index questionnaire expressed in Medians±EE are presented in Table 3. The Wilcoxon ranks test was performed using the SPSS Statistics program considering statistically significant values for a level of $p<0.05$.

TABLE 4

Evaluation of Gabapentin and Fluoxetine for the pain treatment. Helsinki Chronic Pain Index questionnaire

| TIME | G0-D | G1-D |
|---|---|---|
| WEEK 0 | 21.5 ± 2.43 | 22 ± 1.75 |
| WEEK 1 | 20.5 ± 3.66 | 15 ± 3.23 |
| WEEK 2 | 20 ± 3.1 | 20 ± 2.87 |
| WEEK 3 | 15.5 ± 3.1 | 15 ± 3.06 |
| WEEK 4 | 15.5 ± 2.56 | 18 ± 2.98 |
| WEEK 5 | 15 ± 1.54 | 17 ± 3.68 |
| WEEK 6 | 14 ± 2.35 | 18 ± 3.03 |
| WEEK 7 | 13.5 ± 1.55 | 18 ± 2.8 |
| WEEK 8 | 13.5 ± 1.41 | 16 ± 2.42 |

As can be observed, the results obtained with the administration of Gabapentin or Fluoxetine were significantly favorable for the pain treatment once different pain assessment questionnaires were applied, where the dose of useful administration is 0.1 to 2 mg/Kg of Fluoxetine or 1.5 to 10 mg/Kg of Gabapentin.

As a final point to the description of the invention, are presented below the main advantages that in a novel but non-limitative manner show the developed compositions:
Stable composition
Effective and efficient composition
Comprehensive management of epilepsy
Comprehensive management of pain
Use of low doses of gabapentin.
Decrease in the adverse effects of gabapentin.
Composition with less adverse effects compared to compositions with NSAIDs.
Veterinary composition easy to administer.
It does not produce dependence.
Decreases or eliminates the side effects of the active principle.

The invention claimed is:

1. A stable solid veterinary composition for oral administration, wherein the composition is in the form of a segmentable tablet and comprising:
a) gabapentin or a pharmaceutically acceptable salt thereof in a concentration of 1 to 1000 mg; b) from 10% to 80% of the composition total weight of silicon dioxide or colloidal silicon dioxide, in a concentration of no more than 80% of the total weight; c) from 1% to 20% of the total weight of the composition of sorbitan monolaurate; d) from 13.3% to 60.9% of the total weight of the composition of a diluent selected from cellulose microcrystalline, mannitol, lactose and combinations thereof; e) from 1.0% to 14.0% of the total weight of the composition of a disintegrant selected from croscarmellose, crospovidone and a combination thereof; f) one lubricating agent; and g) optionally one coloring agent.

2. A The solid veterinary composition for oral administration according to claim 1, wherein the gabapentin or a pharmaceutically acceptable salt thereof is in a concentration of 100 to 400 mg.

3. The solid veterinary composition for oral administration according to claim 1 or 2, useful for the pain treatment and/or epilepsy wherein the gabapentin or a pharmaceutically acceptable salts thereof is in a dose range of 10 to 20 mg/Kg by weight of the veterinary patient, and preferably in a dose range of 1.5 to 10 mg/Kg by weight of the veterinary patient.

4. The solid veterinary composition for oral administration according to claim 1, wherein the colorant is selected from caramel, ferric oxide, red, yellow, titanium oxide, carmoisine, bluish black of naphthol, erythrosine, amaranth and combinations thereof.

5. The solid veterinary composition for oral administration according to claim 1, wherein optionally contains vitamin B1, vitamin B2, vitamin B12 or the combination thereof.

6. The solid veterinary composition according to claim 1, wherein the tablet is adapted to be segmented into equal parts, and wherein:
   a) Each segment retains a specific amount of gabapentin or a pharmaceutically acceptable salt thereof;
   b) The integrity of the doses is not compromised;
   c) The segmentation of the tablet is made manually or by a mechanical process; and
   d) The segments comprise no more than four and not less than two segments.

7. The solid veterinary composition according to claim 1, and which wherein the composition is useful for treating pain and/or epilepsy in mammalian animals of different weight and/or size.

8. The solid veterinary composition according to claim 1, wherein the composition is useful for treating pain or epilepsy in companion animals with different weight and/or size.

9. The solid veterinary composition according to claim 1, useful for the treatment of mild, moderate and/or severe pain.

10. The solid veterinary composition according to claim 1, useful for the treatment of epilepsy.

* * * * *